United States Patent
Wächtler et al.

[11] Patent Number: 5,340,497
[45] Date of Patent: Aug. 23, 1994

[54] FLUOROPHENYLPYRIMIDINES

[75] Inventors: Andreas Wächtler, Griesheim; Hans-Michael Kompter, Weiterstadt; Eike Poetsch, Möhltal; Thomas Geelhaar, Mainz; Reinhard Hittich, Modautal; Joachim Krause, Dieburg, all of Fed. Rep. of Germany

[73] Assignee: Merck Patent Gesellschaft Mit Beschrankter Haftung, Darmstadt, Fed. Rep. of Germany

[21] Appl. No.: 26,243

[22] Filed: Mar. 1, 1993

Related U.S. Application Data

[63] Continuation of Ser. No. 572,980, Aug. 2, 1990, abandoned.

[30] Foreign Application Priority Data

Jun. 6, 1989 [DE] Fed. Rep. of Germany ....... 3919104

[51] Int. Cl.$^5$ ................... C09K 19/34; C07D 239/02
[52] U.S. Cl. ................... 252/299.61; 514/298
[58] Field of Search ............... 544/298; 252/299.61

[56] References Cited

U.S. PATENT DOCUMENTS

| | | | |
|---|---|---|---|
| 4,709,030 | 11/1987 | Petrzilka et al. | 544/242 |
| 4,808,333 | 2/1989 | Huynh-ba et al. | 252/299.66 |
| 4,820,839 | 4/1989 | Krause et al. | 544/316 |
| 4,834,904 | 5/1989 | Krause et al. | 252/299.01 |
| 4,973,426 | 11/1990 | Ohno et al. | 252/299.66 |
| 5,021,191 | 6/1991 | Saito et al. | 252/299.61 |
| 5,047,170 | 9/1991 | Huynh-ba et al. | 252/299.6 |
| 5,059,340 | 10/1991 | Miyazawa et al. | 252/299.61 |
| 5,089,168 | 2/1992 | Krause et al. | 252/299.61 |

FOREIGN PATENT DOCUMENTS 8707890  12/1987  PCT Int'l Appl.

*Primary Examiner*—Robert L. Stoll
*Assistant Examiner*—C. Harris
*Attorney, Agent, or Firm*—Millen, White, Zelano, & Branigan

[57] ABSTRACT

The invention relates to fluorophenylpyrimidines of the formula I:

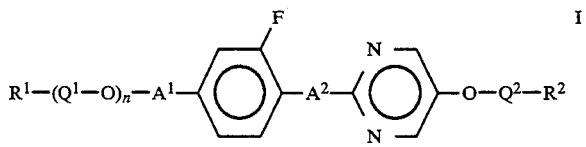

where
R$^1$, R$^2$, A$^1$, A$^2$, Q$^1$, Q$^2$ and n have the meaning specified in patent claim 1, and to their use as components of liquid-crystalline, in particular ferroelectric, media.

9 Claims, No Drawings

FLUOROPHENYLPYRIMIDINES

This application is a continuation of application Ser. No. 07/572,980, filed Aug. 2, 1990, now abandoned.

The invention relates to fluorophenylpyrimidines the formula I:

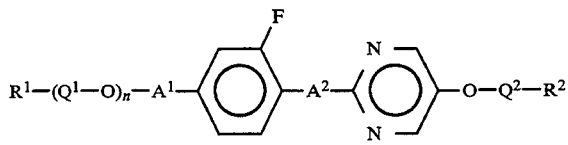

where $Q^1$ $Q^2$ are, in each case independently of each other, CO or $CH_2$, n is 0 or 1, $A^1$ and $A^2$ are, in each case independently of each other, 1,4-phenylene or a single bond, and $R^1$ and $R^2$ are, in each case independently of each other, an unsubstituted alkyl or alkenyl radical or an alkyl or alkenyl radical substituted by CN or by at least one halogen, which radical contains up to 18 carbon atoms and in which radical one or more $CH_2$ groups may be replaced by a radical selected from the group comprising —O—, —CO—O—, —O—CO— or —C—C—, two oxygen atoms not being adjacent, and in the case where n=1, one of the radicals $R^1$ and $R^2$ may also be a group of the formula II:

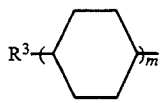

in which $R^3$ is an unsubstituted alkyl, alkenyl or alkoxy group or an alkyl, alkenyl or alkoxy group substituted by CN or by at least one halogen, which group contains up to 18 carbon atoms, and m is 1 or 2.

Chiral tilted smectic liquid-crystalline phases having ferroelectric properties can be prepared by adding one or more tilted smectic phases containing a suitable chiral additive to basic mixtures (L. A. Beresnev et al., Mol. Cryst. Liq. Cryst. 89, 327 (1982); H. R. Brand et al., J. Physique 44 (lett.), L 771 (1983). Such phases can be used as dielectrics for fast switching displays which are based on the principle of SSFLC technology, described by Clark and Lagerwall (N. A. Clark and S. T. Lagerwall, Appl. Phys. Lett. 36, 899 (1980); U.S. Pat. No. 4,367,924), based on the ferroelectric properties of the chiral tilted phase. In this phase, the elongated molecules are arranged in layers, the molecules having an angle of tilt with respect to the layer normal. On progressing from layer to layer, the direction of tilt changes by a small angle with reference to an axis perpendicular to the layers, with the result that a helical structure is formed. In displays based on the principle of SSFLC technology, the smectic layers are arranged perpendicularly to the plates of the cell. The helix-like arrangement of the directions of tilt of the molecules is suppressed by a very small spacing of the plates (approximately 1-2 μm). This forces the long axes of the molecules to arrange themselves in a plane parallel to the plates of the cell, as a result of which two distinct tilt orientations are produced. By applying a suitable electrical alternating field it is possible to switch back and forth between these two states in the liquid-crystalline phase, which has a spontaneous polarization. This switching operation is substantially faster than in conventional twisted cells (TN LCDs) based on nematic liquid crystals.

A great disadvantage for many applications of the currently available materials having chiral tilted smectic phases (such as, for example, $S_C^*$, but also $S_H^*$, $S_I^*$, $S_J^*$, $S_K^*$, $S_G^*$, $S_F^*$) is their low chemical and thermal stability and low photostability. A further disadvantageous property of displays based on currently available chiral tilted smectic mixtures is that the spontaneous polarization has unduly low values, with the result that the switching time behavior of the displays is unfavorably affected and/or the pitch and/or the tilt and/or the viscosity of the phases does not meet the requirements of display technology. In addition, the temperature range of the ferroelectric phases is unduly small and is predominantly at unduly high temperatures.

It has now been found that the use of compounds of the formula I as components of chiral tilted smectic mixtures can substantially reduce the disadvantages mentioned. The compounds of the formula I are consequently eminently suitable as components of chiral tilted smectic liquid-crystalline phases. In particular, it is possible to use them to prepare chiral tilted smectic liquid-crystalline phases which are particularly stable chemically and have beneficial ferroelectric phase ranges, beneficial ranges for the viscosity, in particular wide $S_C^*$ phase ranges, outstanding supercooling capability down to temperatures below 0° C. without crystallization occurring and spontaneous polarization values which are high for such phases. P is the spontaneous polarization in $nC/cm^2$. The compounds of the formula I are, however, also suitable for liquid-crystalline phases for the electroclinic effect.

The compounds of the formula I have a neutral anisotropy of the relative permittivities (Δε=−0.2 to +0.5) and therefore have a wide field of application. Depending on the choice of the substituents, these compounds may be used as basic materials of which liquid-crystalline smectic phases are predominantly composed; however, compounds of the formula I may also be added to liquid-crystalline basic materials selected from other compound classes in order to vary, for example, the dielectric and/or optical anisotropy and/or the viscosity and/or the spontaneous polarization and/or the phase ranges and/or the angle of tilt and/or the pitch of such a dielectric.

DE 3,315,295 specifies a very wide general formula for nematic fluorophenylpyrimidines which encompasses some of the compounds of the formula I claimed here. In DE 3,315,295 there are no references of any kind to $S_C$ compounds of this type, it being intended, on the contrary, to suppress the smectic phases in particular. No individual compounds of the formula claimed here are mentioned therein either.

Chiral dopants for ferroelectric mixtures are claimed in EP-A-0,278,665 whose wide general formula encompasses the compounds according to the invention. In compounds mentioned therein, however, the lateral halogen substituent on the phenyl ring is always in the meta position with respect to the pyrimidine ring. However, these have a positive Δε and are therefore less suitable for ferroelectric mixtures.

JP 63-253,075 describes similar compounds of the formula

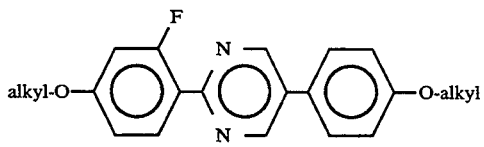

but these have relatively high phase transitions.

The person skilled in the art was consequently not able either to infer from the prior art in a simple manner synthesis possibilities for the compounds claimed or to perceive that the compounds according to the invention have predominantly wide and beneficially situated $S_C$ phases and are also distinguished by beneficial values for the rotational viscosity.

The invention consequently relates to the fluorophenylpyrimidines of the formula I, in particular of the formulae I1, I2 and I3, in which m and o are each 1 to 18.

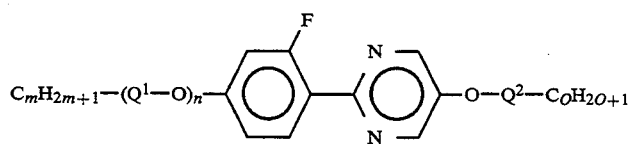

I1

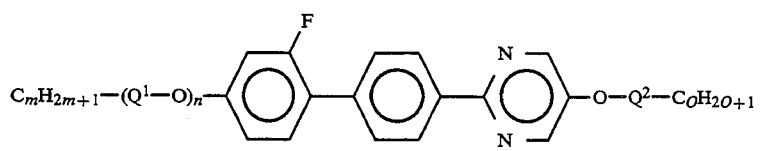

I2

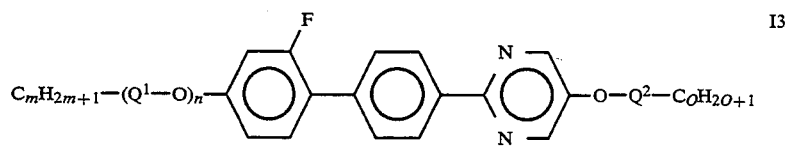

I3

The invention relates, in particular, to those optically active fluorophenylpyrimidines of the formula I* in which one of the radicals $R^1$ and $R^2$ is a chiral group of the formula III:

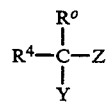

III where
$R^4$ is a group of the formula

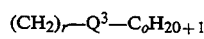

$(CH_2)_r-Q^3-C_oH_{2o+1}$ in which
$Q^3$ is —O—, —O—CO— or a single bond,
r is 0, 1 or 2, and
O is 1 to 7,
Y is CN, halogen or $CH_3$,
Z is a single bond or —$(CH_2)_p$— in which one $CH_2$ group may be replaced by —O—, —O—CO— or —CO—O— and p is 1, 2, 3, 4, 5 or 6, and $R^0$ is H or $CH_3$,
with the proviso that $R^0$ is different from Y.

The invention further relates to ferroelectric liquid-crystalline phases having a content of at least one compound of the formula I and also to liquid-crystal display components, in particular ferroelectric electro-optical display components, which contain such phases.

The phases according to the invention contain preferably at least two, and in particular, at least three compounds of the formula I. Particularly preferred are chiral tilted smectic liquid-crystalline phases according to the invention whose achiral basic mixture contains, in addition to compounds of the formula I, at least one other component having negative dielectric anisotropy or positive dielectric anisotropy which is small in magnitude. This further component or these further components of the achiral basic mixture may form 1% to 50%, preferably 10 to 25%, of the basic mixture. Suitable further components having positive or negative dielectric anisotropy which is small in magnitude are compounds of the formula IV which encompasses compounds of the subformulae IVa to IVi:

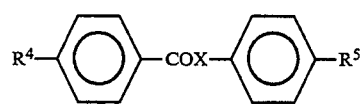

IVa

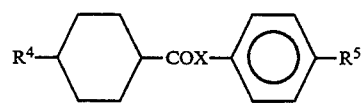

IVb

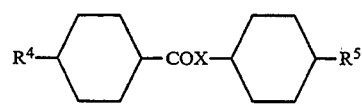

IVc

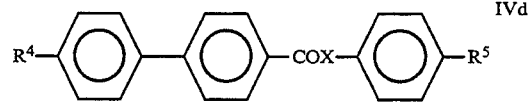

IVd

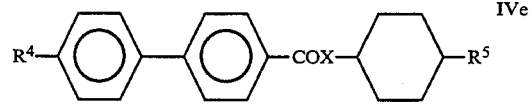

IVe

-continued

IVf: R⁴—⌬—COX—⌬—⌬—R⁵

IVg: R⁴—⬡—COX—⌬—⌬—R⁵

R⁴ and R⁵ are in each case preferably straight-chain alkyl, alkoxy, alkanoyloxy or alkoxycarbonyl containing in each case 3 to 12 carbon atoms. X is preferably oxygen. In the compounds of the formulae IVa, IVb, IVd, IVe, IVf and IVg, a 1,4-phenylene group may also be laterally substituted by halogen or CN, in particular, preferably by fluorine.

Particularly preferred are the compounds of the subformulae IVa, IVb, IVd and IVf in which R⁴ and R⁵ are in each case straight-chain alkyl or alkoxy containing in each case 5 to 10 carbon atoms.

Particularly preferred individual compounds are specified in Table I below:

TABLE I

| Formula | R⁴ | R⁵ | X |
|---|---|---|---|
| IVa | n-decyloxy | n-heptyloxy | O |
| IVa | n-hexyloxy | n-decyloxy | O |
| IVa | n-octyloxy | n-heptyl | O |
| IVa | n-octyloxy | n-pentyl | O |
| IVa | n-decloxy | n-heptyl | O |
| IVa | n-decyloxy | n-pentyl | O |
| IVf | n-pentyl | n-pentyl | O |
| IVf | n-pentyl | n-hexyl | O |

The compounds of the subformulae IVc, IVh and IVi are suitable as additives for lowering the melting point and are normally added to the basic mixtures in an amount of not more than 5%, preferably 1 to 3%. R⁴ and R⁵ in the compounds of the subformulae IVc, IVh and IVi are preferably straight-chain alkyl containing 2 to 7, preferably 3 to 5, carbon atoms. A further class of compound which is suitable for lowering the melting point in the phases according to the invention is that of the formula:

R⁴—⬡—⌬—OOC—R⁵ in which R⁴ and R⁵ have the preferred meaning specified for IVc, IVh and IVi.

Further suitable components having negative dielectric anisotropy are furthermore compounds containing the structural element A, B or C.

A: —⬡(CN)—
B: —CH₂—CH(CN)—
C: —CH(Cl)—

Preferred compounds of this type correspond to the formulae Va, Vb and Vc:

Va: R'—Q¹—⬡(CN)—Q²—R"

Vb: R'—Q¹—CH₂—CH(CN)—Q²—R"

Vc: R'—Q³—Q⁴—R'''

R' and R" are in each case preferably straight-chain alkyl or alkoxy groups containing in each case 2 to 10 carbon atoms. Q¹ and Q² are in each case 1,4-phenylene, trans-1,4-cyclohexylene, 4,4'-biphenylyl, 4-(trans-4-cyclohexyl)phenyl, trans,trans-4,4'-bicyclohexyl or one of the groups Q¹ and Q² is also a single bond.

Q³ and Q⁴ are in each case 1,4-phenylene, 4,4'-biphenylyl or trans-1,4-cyclohexylene. One of the groups Q³ and Q⁴ may also be 1,4-phenylene in which at least one CH group is replaced by N. R''' is an optically active radical containing an asymmetric carbon atom of the structure —CH*(Cl)—  or  —CH*(CN)—.

Particularly preferred compounds of the formula Vc are those of the formula Vc':

Vc': Alkyl—(A)ₙ—⌬(N,N)—⌬—R''' in which A is 1,4-phenylene or trans-1,4-cyclohexylene and n is 0 or 1.

Particularly preferred are those ferroelectric liquid-crystalline phases having a content of at least one achiral fluorophenylpyrimidine of the formula I1, at least one achiral phenylpyrimidine of the formula Vc' in which R''' is an alkyl or alkoxy radical containing up to 18 carbon atoms as basic material having a wide S_C phase and at least one chiral fluorophenylpyrimidine of the formula I* as optically active dopant. Those ferroelectric liquid-crystalline phases are furthermore preferred which contain, in addition to the specified compounds of the formula I1, Vc' and I*, at least one phenylpyridine of the formula Vd and/or a 2,3-difluorophenylpyrimidine of the formula Ve and/or a phenylpyrimidine of the formula Vf:

Vd: R'—⌬—⌬(N)—R"

Ve: R'—⌬(F,F)—⌬(N,N)—R"

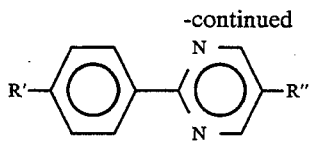

The nonchiral fluorophenylpyrimidines of the formula I4

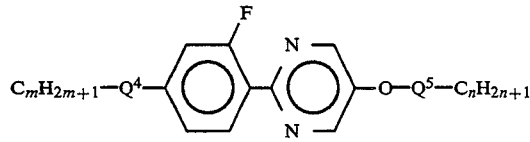

in which m and n are, in each case independently of each other, 1 to 18,
$Q^4$ is —O— or a single bond and
$Q^5$ is —CO—,

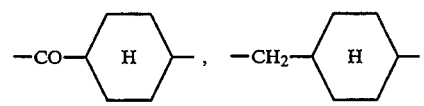

or a single bond,
are particularly suitable as components of smectic basic materials.

The compounds of the formula I4 encompass the nonchiral preferred binuclear and trinuclear materials of the formulae Ia to If listed below.

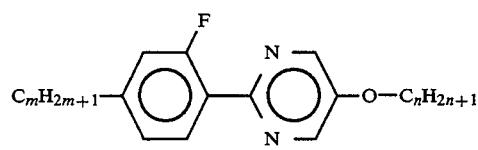

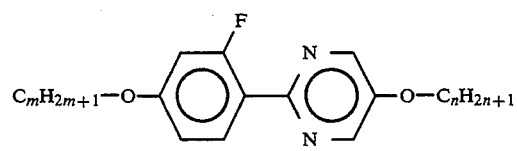

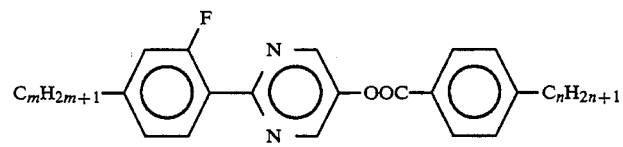

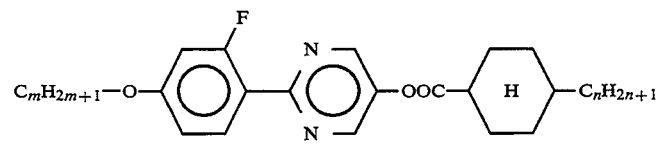

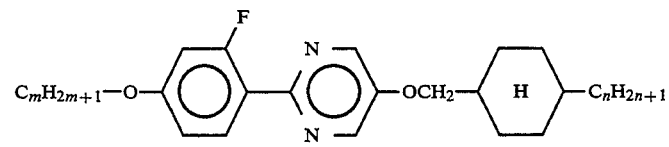

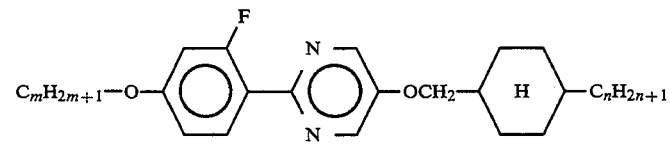

The compounds of the formulae I2 and I3 encompass the nonchiral preferred compounds of the formulae Ig to Ij listed below.

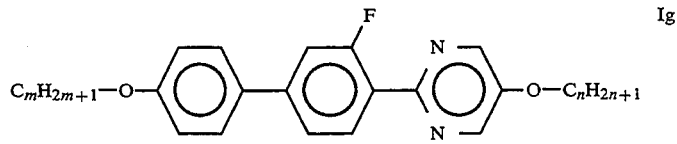

-continued

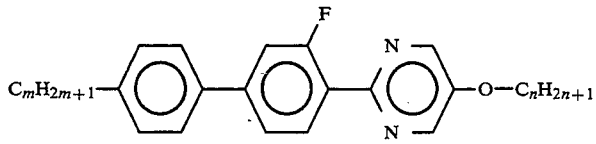
Ih

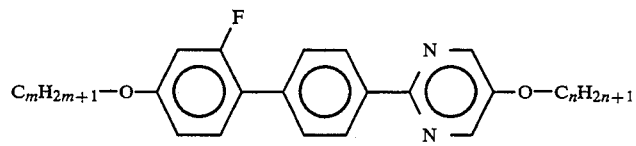
Ii

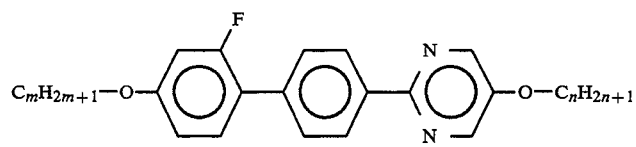
Ij

Among these, those of the subformulae Ia and Ib are particularly preferred.

m is preferably 5 to 14, in particular 6 to 12. n is preferably 3 to 12. The radicals $C_mH_{2m+1}$ and $C_nH_{2n+1}$ are preferably straight-chain. Compounds of the formula I having relatively short radicals of this type are also suitable as components of nematic phases.

The chiral fluoropyrimidines of the formula I* in which one of the radicals $R^1$ and $R^2$ is a group of the formula III are outstandingly suitable as dopants for inducing ferroelectricity in a smectic basic material. They are distinguished, in particular, by a high spontaneous polarization.

Furthermore, they do not destabilize the smectic phase of these basic materials. The radical of the formula III is denoted below by R*.

The chiral compounds of the formula I* accordingly encompass the compounds of the subformulae Ik to Ip containing 2 rings:

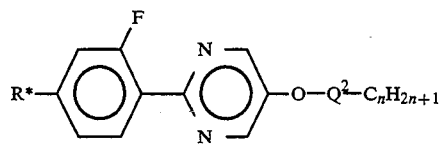
Ik

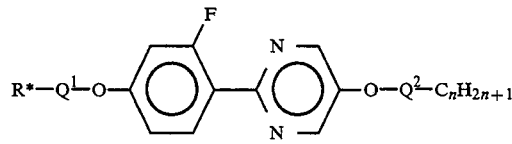
Il

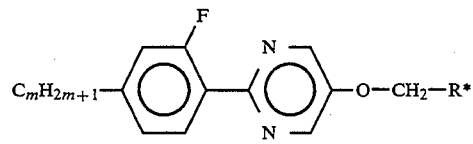
Im

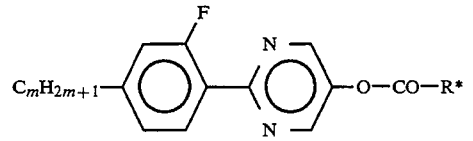
In

-continued

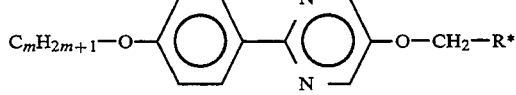
Io

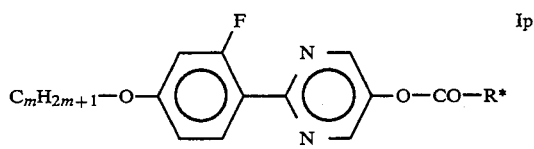
Ip and also the compounds of the formulae Iq to Iw containing 3 rings:

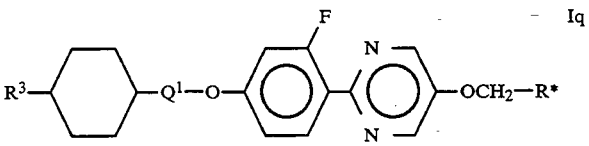
Iq

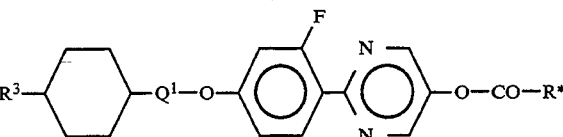
Ir

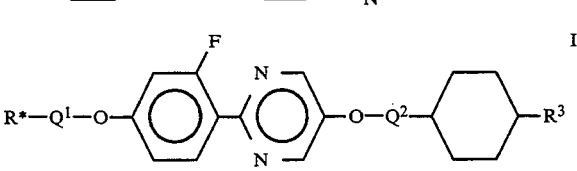
Is

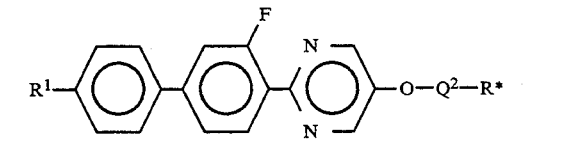
It

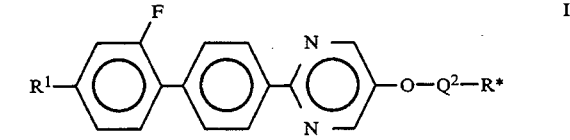
Iu

-continued

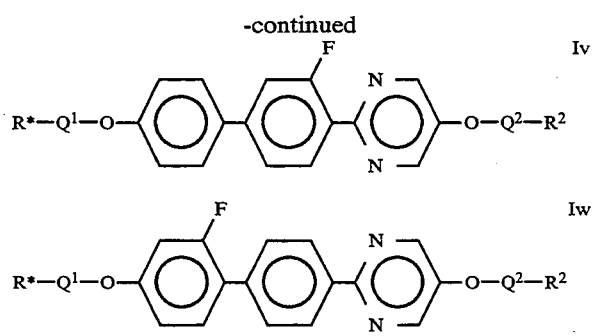

in which m and n have the preferred meanings specified for the compounds of the formulae Ia to Ih.

Preferred in particular are those of the subformulae Ik and Io.

Among these, those chiral compounds of the formula I are particularly preferred in which R* is a group of the formula IIIa:

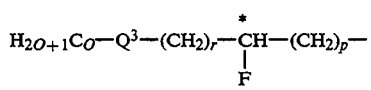  IIIa in which O and $Q^3$ have the specified meaning, r is 1 or 2 and p is 0 or 1.

The chiral radicals of the formula IIIa according encompass the chiral monofluoroalkyl, monofluorooxaalkyl and alkanoyloxymonofluoroalkyl group $R_f^*$ of the formulae IIIa1 to IIIa6:

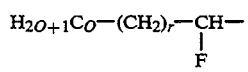 IIIa1

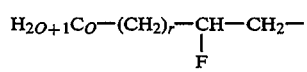 IIIa2

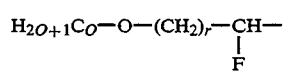 IIIa3

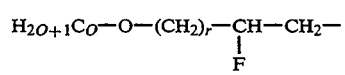 IIIa4

$H_{2O+1}C_O$—CO—O—$(CH_2)_r$—CH—  IIIa5
　　　　　　　　　　　　　　｜
　　　　　　　　　　　　　　F $H_{2O+1}C_O$—CO—O—$(CH_2)_r$—CH—$CH_2$—  IIIa6
　　　　　　　　　　　　　　｜
　　　　　　　　　　　　　　F

Of the chiral monofluoro groups $R_f^*$ of the formulae IIIa1 to IIIa6, those of the formulae IIIa1, IIIa3, and IIIa5 are particularly preferred, in particular those in which r is 2.

Those chiral compounds of the formula I are furthermore preferred in which R* is a group of the formula IIIb

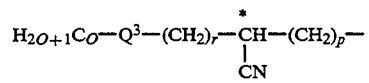  IIIb in O and $Q^3$ have the specified meaning, r is 1 or 2 and p is 0 or 1.

The compounds of the formula I are prepared by methods known per se such as those described in the literature (for example in the standard works such as Houben-Weyl, Methoden der Organischen Chemie (Methods of Organic Chemistry), Georg-Thieme-Verlag, Stuttgart).

The starting substances may, if desired, also be formed in situ so that they are not isolated from the reaction mixture but are immediately converted further to form the compounds of the formula I.

The compounds according to the invention can be prepared by the following reaction scheme.

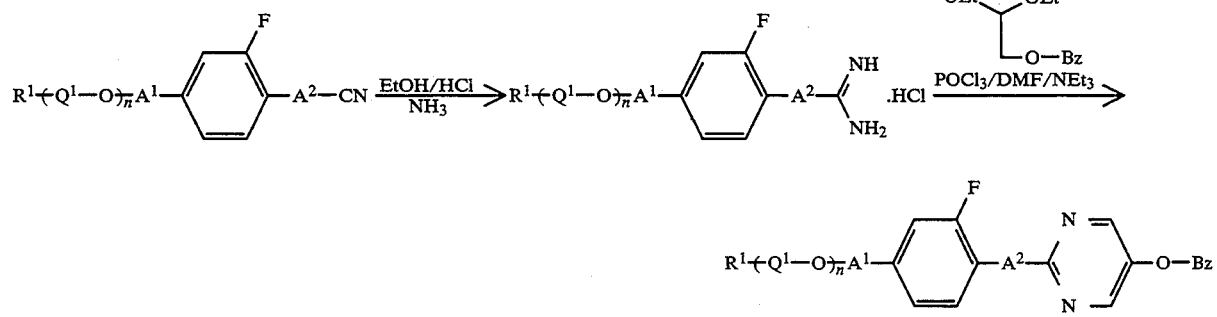

The benzyl group can be split off hydrogenolytically and the hydroxyl group then etherified or esterified again by known methods.

Thus, to prepare compounds of the formula I2 in which r=2, suitable precursors can be prepared from optically active malic acid by reaction scheme I below:

Scheme I

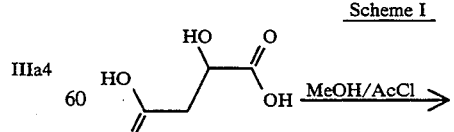

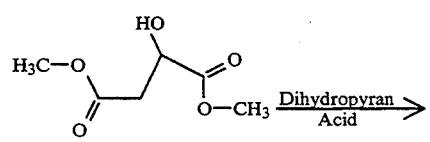

13
-continued
Scheme I

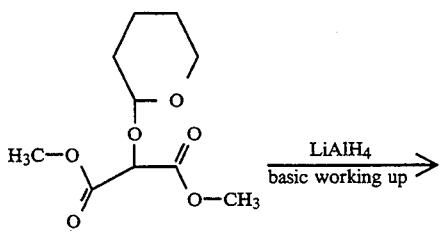

14 ification, the isopropylidene ketal is hydrolyzed under standard conditions to the 1,2-diol and this can then be converted into the corresponding epoxide in accordance with the reaction conditions of Di Fabio and Misiti (R. Di Fabio and D. Misiti, Gazetta Chimica Italiana 118, 209–210 (1988)).

The treatment of the acetonide with HBr/glacial acetic acid and the subsequent reaction of the bromooxyalkyl acetates obtained in this manner with potassium pentanolate also yields, according to the work of U. Schmidt et al., the desired epoxides according to Scheme II (U. Schmidt, J. Tabiersky, F. Bartowiak and J. Wild, Angew. Chem. 92, 201–202 (1980)).

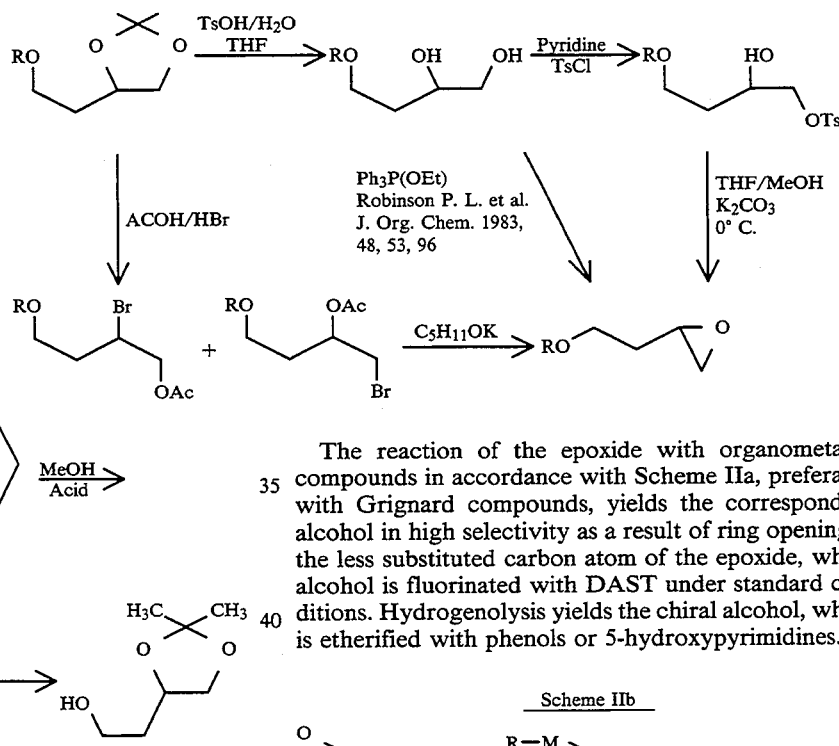

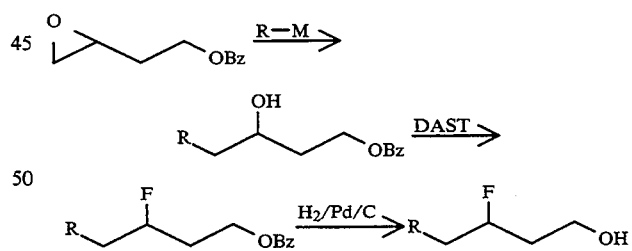

Up to this stage, the synthesis due to Mori et al. has been described (K. Mori, T. Takigawa and T. Matsuo, Tetrahedron 35, 933–944 (1979)).

Later Meyers and Lawson then found that the chemical purity of the acetonide obtained in this way is only about 90% (A. I. Meyers and J. P. Lawson, THL 23 4883–4886 (1982)).

Regardless of this, the free alcohol group of the acetonide can be etherified by one of the usual methods (for example, C. A. Brown and D. Barton, Synthesis (1974) 434 or B. R. Jursic, Tetrahedron 44, 6677–6680 (1988)).

The benzyl ether (K. Isaac and P. Kocienski, J. Chem. Soc., Chem. Commun. (1982) 460–462) is suitable in particular as a protective group since it can be easily split off later hydrogenolytically. After the etherification The reaction of the epoxide with organometallic compounds in accordance with Scheme IIa, preferably with Grignard compounds, yields the corresponding alcohol in high selectivity as a result of ring opening at the less substituted carbon atom of the epoxide, which alcohol is fluorinated with DAST under standard conditions. Hydrogenolysis yields the chiral alcohol, which is etherified with phenols or 5-hydroxypyrimidines.

If the epoxide is opened with pyridine/HF (N. Mongelli, F. Animati et al., Synthesis 310 (1988)), the corresponding fluoroalcohol is obtained which can then be converted into the corresponding tosylate. Such tosylates are suitable, in particular, for alkylating phenols and 5-hydroxypyrimidines in accordance with Scheme III or Scheme IV.

Scheme III

-continued

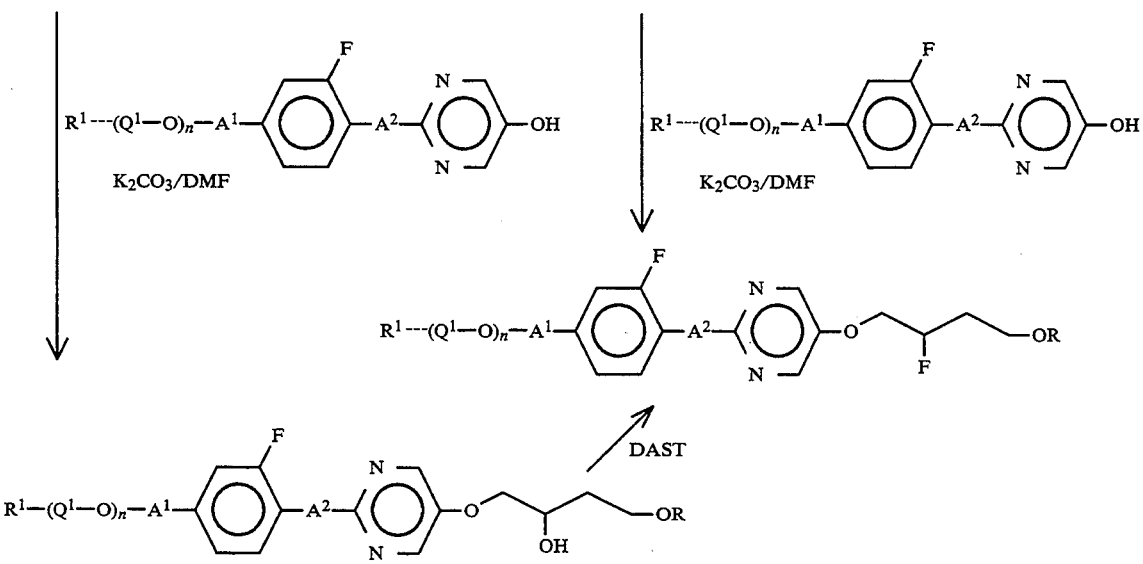

Scheme IV

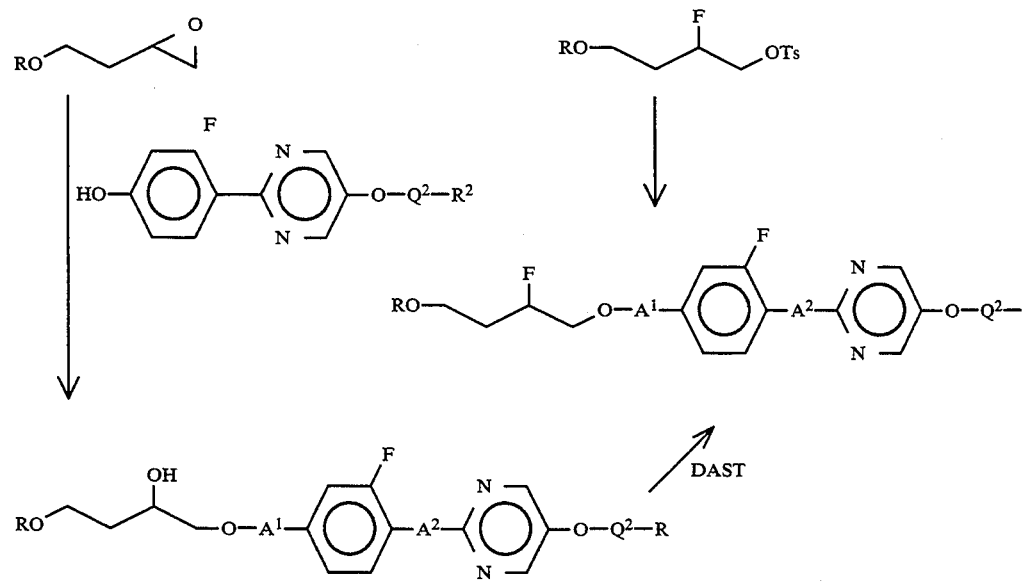

As the above reaction schemes show, the epoxide may also be reacted directly with phenols. The epoxide is opened with high selectivity at the less substituted carbon atom to form the chiral secondary alcohol which is then converted with DAST into the compounds according to the invention, this being accompanied by inversion. For the usual reactions of alcohols with DAST, see M. Hudlicky, Organic Reactions 35, 513–637 (1987).

The compounds according to the invention in which $Q^3 = -O-CO-$ can be prepared from the corresponding benzyl ethers by hydrogenolysis and subsequent esterification. The following synthesis scheme V describes the preparation:

Scheme V

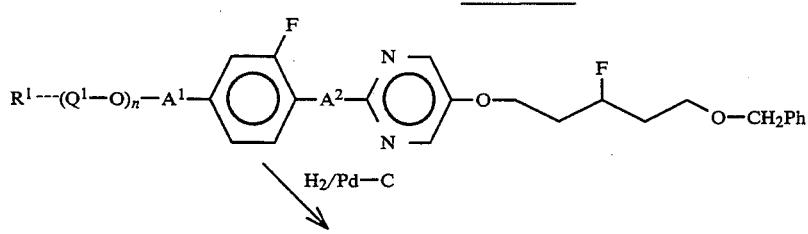

-continued
Scheme V

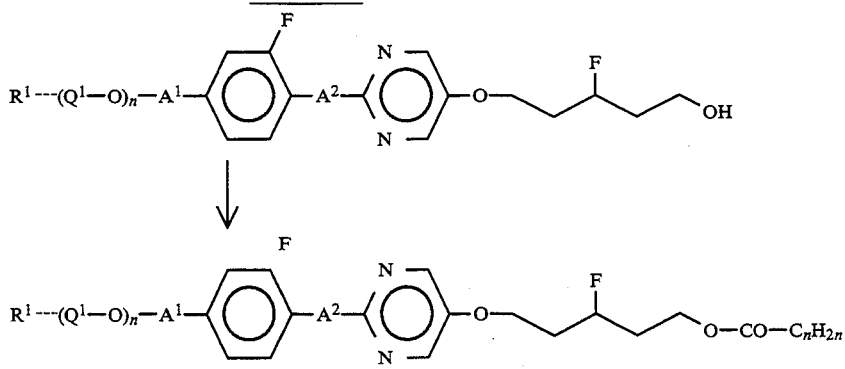

The compounds in which $Q^3$=—O—CO— are furthermore obtained by oxidizing the corresponding fluoroalcohols and then esterifying with mesogenic phenols in accordance with Scheme VI:

Scheme VI

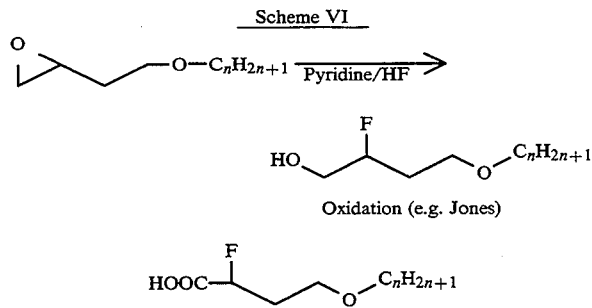

Oxidation (e.g. Jones)

If a racemization occurs during the oxidation, the optically active fluoroacids can be obtained by Helmchen racemate resolution (Angew. Chem. 91, 65 (1979)).

CH-azide compounds such as, for example, 2-fluorotolunitrile also open the epoxide in the presence of suitable bases to form the optically active secondary alcohol which is then fluorinated with DAST, this being accompanied by inversion. Preferred reaction routes can be inferred from the following Scheme VII.

Scheme VII

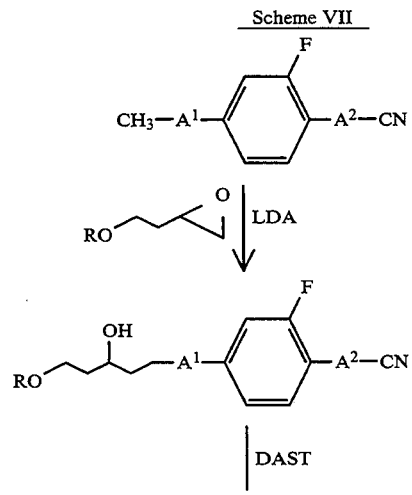

-continued
Scheme VII

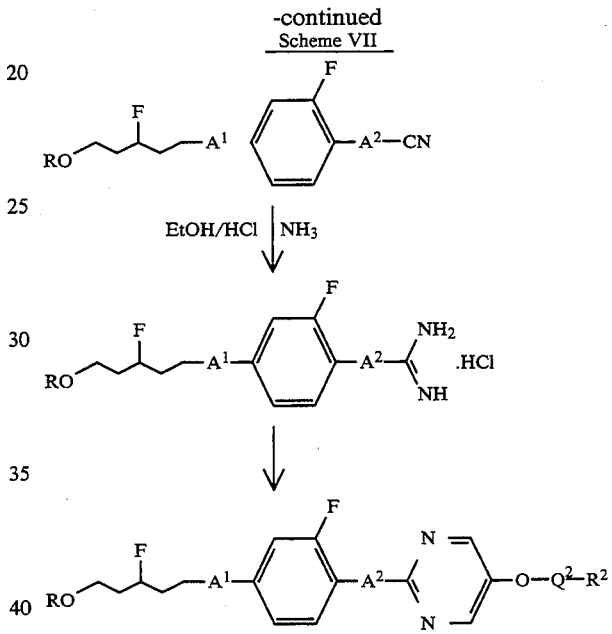

The compounds of the formula I in which r=1 can be prepared analogously using the known epoxides of the formula

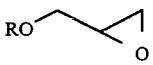

or the fluoroalcohols of the formula

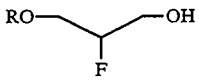

which can be obtained from these by standard methods.

The compounds of the formula I are also suitable as components of nematic liquid-crystalline phases, for example for avoiding reverse twist.

These liquid-crystalline phases according to the invention are composed of 2 to 25, preferably 3 to 15, components, including at least one compound of the formula I. The other components are preferably selected from the nematic or nematogenic substances, in particular the known substances from the classes comprising the azoxybenzenes, benzylideneanilines, biphenyls, terphenyls, phenylbenzoates or cyclohexylbenzoates, phenyl cyclohexanecarboxylates or cyclohexyl cyclohexanecarboxylates, phenylcyclohexanes, cyclohexylbiphenyls, cyclohexylcyclohexanes, cyclohexylnaphthalenes, 1,4-biscyclohexylbenzenes, 4,4'-biscyclohexylbiphenyls, phenylpyrimidines or cyclohexylpyrimidines, phenylpyridazines or cyclohexylpyridazines and also their N-oxides, phenylhexyldioxanes or cyclohexyldioxanes, phenyl-1,3-dithianes or cyclohexyl-1,3-dithianes, 1,2-diphenylethanes, 1,2-dicyclohexylethanes, 1-phenyl-2-cyclohexylethanes, optionally halogenated stilbenes, benzyl phenyl ethers, tolanes or substituted cinnamic acids.

The most important compounds which are suitable as components of such liquid-crystalline phases can be characterized by the formula I':

R'—L—G—E—R''  I' where
L and E are each a carbocyclic or heterocyclic ring system composed of the group formed from 1,4-disubstituted benzene rings and cyclohexane rings, 4,4'-disubstituted biphenyl, phenylcyclohexane and cyclohexylcyclohexane systems, 2,5-disubstituted pyrimidine rings and 1,3-dioxane rings, 2,6-disubstituted naphthalene, diand tetrahydronaphthalene, quinazoline and tetrahydroquinazoline,
G is

| —CH=CH— | —N(O)=N— |
| —CH=CY— | —CH=N(O)— |
| —C≡C— | —CH$_2$—CH$_2$— |
| —CO—O— | —CH$_2$—O— |
| —CO—S— | —CH$_2$—S— |
| —CH=N— | —COO—Phe—COO— | or a C—C single bond,
Y is halogen, preferably chlorine, or —CN, and R' and R'' are alkyl, alkoxy, alkanoyloxy, alkoxycarbonyl or alkoxycarbonyloxy containing up to 18, preferably up to 8, carbon atoms, or one of these radicals is also CN, NC, NO$_2$, CF$_3$, F, Cl or Br.

In most of these compounds, R' and R'' are different from each other, one of these radicals usually being an alkyl group or alkoxy group. However, other variants of the substituents envisaged are also common. Many such substances or even mixtures thereof are obtainable commercially. All these substances are obtainable by methods known in the literature.

The phases according to the invention contain about 0.1 to 99, preferably 10 to 95%, of one or more compounds of the formula I. Liquid-crystalline phases according to the invention containing 0.1-40, preferably 0.5-30%, of one or more compounds of the formula I are furthermore preferred.

The phases according to the invention are prepared using methods which are standard per se. As a rule, the components are dissolved in one another, expediently at elevated temperature.

The liquid-crystalline phases according to the invention can be modified by suitable additives in such a way that they can be used in all the types of liquid-crystal display components hitherto known.

Such additives are known to the person skilled in the art and are described in detail in the literature. For example, conducting salts, preferably ethyldimethyldodecylammonium 4-hexyloxybenzoate, tetrabutylammonium tetraphenylboranate or complex salts of crown ethers (cf. for example, I. Haller et al., Mol. Cryst. Liq. Cryst. volume 24, pages 249–258 (1973)) may be added to improve the conductivity, pleochroic dyestuffs may be added to produce colored guest-host systems or substances may be added to alter the dielectric anisotropy, the viscosity and/or the orientation of the nematic phases.

Such substances are described, for example, in German Offenlegungsschrift 2,209,127, 2,240,864, 2,321,632, 2,338,281, 2,450,088, 2,637,430, 2,853,728 and 2,902,177.

The following examples are intended to illustrate the invention without restricting it. m.p.=melting point and c.p.=clear point. Above and below percentage data are percentages by weight; all temperatures are specified in degrees Celsius. "Standard working-up" means that water is added, extraction is carried out with methylene chloride, isolation is carried out, the organic phase is dried and evaporated down, and the product is purified by crystallization and/or chromatography.
Furthermore
C denotes crystalline,
N denotes nematic
S denotes smectic
I denotes isotropic.
The numbers appearing between these symbols specify the phase transition temperature in °C. in each case.
The following abbreviations are furthermore used:
DAST: diethylaminosulfur trifluoride
DMF: dimethylformamide
n-BuLi: n-butyllithium

EXAMPLE 1

0.185 mol of DMF is added to 0.15 mol of POCl$_3$ while cooling. After 15 minutes, a solution of 0.1 mol of benzyloxyacetaldehyde diethyl acetal in 50 ml of DMF is added and the mixture is then heated to 50° C. After 12 hours, the reaction mixture is cooled to room temperature and 0.1 mol of 4-heptyloxy-2-fluorobenzamidine hydrochloride is added. The temperature rises under these conditions to about 40° C. The reaction mixture is stirred for 30 minutes, then 110 ml of triethylamine are added. The temperature rises under these conditions to about 70° C, and the reaction mixture becomes viscous. To improve the stirrability, the reaction mixture may be diluted with DMF. The triethylamine is then distilled off, the residue is allowed to cool to about 100° C, 500 ml of water are then added and the mixture is acidified with concentrated HCl. The precipitate produced under these conditions is filtered off by suction, thoroughly washed with water and dried in vacuo. The benzyloxy compound thus obtained is taken up in THF and hydrogenated at room temperature without the use of pressure using a Pd catalyst (Pd-C-5% E101RW). After removing the catalyst, the solution is evaporated down in vacuo, the hydroxypyrimidine is taken up in methyl ethyl ketone and boiled for 12 hours under reflux in the presence of an equivalent amount of dried potassium carbonate and bromononane. The standard working-up yields 2-(4-heptyloxy-2-fluorophenyl)-5-nonyloxypyrimidine having the following phase transitions: C 39 S$_C$ 60 N 73.1, Δε= —0.1.

The following compounds of the formula I4 are prepared analogously:

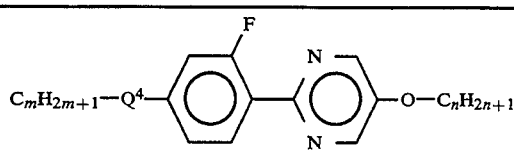

| m | Q⁴ | n | C | $S_c$ | N | I | Δε |
|---|----|----|-----|------|------|-----|------|
| 7 | 0 | 8 | 39 | 49 | 73.6 | | −0.1 |
| 7 | 0 | 10 | 41 | 69 | 76.1 | | −0.1 |
| 7 | 0 | 11 | 56 | 73 | 75.3 | | −0.1 |
| 7 | 0 | 12 | 47 | 77 | 77.6 | | 0.0 |
| 8 | 0 | 8 | 42 | 52 | 77.3 | | −0.1 |
| 8 | 0 | 9 | 39 | 62 | 75.4 | | −0.1 |
| 8 | 0 | 10 | 40 | 72 | 78.2 | | −0.1 |
| 8 | 0 | 11 | 49 | 76 | 77.9 | | 0.0 |
| 8 | 0 | 12 | 51 | 80 | — | | 0.0 |
| 10 | 0 | 8 | 48 | 58 | 77.2 | | 0.0 |
| 10 | 0 | 9 | 45 | 67 | 76.4 | | +0.1 |
| 10 | 0 | 10 | 45 | 75 | 79.2 | | +0.1 |
| 10 | 0 | 11 | 50 | 79 | 79.6 | | +0.1 |
| 10 | 0 | 12 | 54 | 82,6 | — | | 0.0 |
| 12 | 0 | 8 | 51 | 62 | 76 | | +0.1 |
| 12 | 0 | 9 | 49 | 69 | 75.9 | | 0.0 |
| 12 | 0 | 10 | 52 | 77 | 79.1 | | +0.1 |
| 12 | 0 | 11 | 58 | 80 | — | | +0.1 |
| 12 | 0 | 12 | 61 | 84 | — | | +0.5 |
| 8 | 0 | OCH₂–[H]– | | | 3 | | |
| 8 | 0 | OCH₂–[H]– | | | 4 | | |
| 8 | 0 | OCH₂–[H]– | | | 5 | | |
| 8 | 0 | OCH₂–[H]– | | | 7 | | |
| 7 | 0 | OCH₂–[H]– | | | 3 | | |
| 7 | 0 | OCH₂–[H]– | | | 4 | C 92 $S_A$ 141 N 152 9 I, | | |
| 7 | 0 | OCH₂–[H]– | | | 5 | | |
| 7 | 0 | OCH₂–[H]– | | | 7 | | |
| 7 | 0 | OCH₂–[H]– | | | 8 | C 99 $S_A$ 150 I | | |

The compounds of the formula I2 are obtained analogously from 2-(4′-alkyl-2-fluoro-4-biphenylyl)-5-hydroxypyrimidines (prepared from 4′-alkyloxy-2fluoro-4-biphenylylcarbamidines in accordance with Example 1).

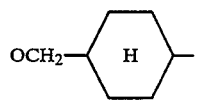

| m | Q⁴ | n |
|---|----|----|
| 8 | 0 | 7 |
| 8 | 0 | 8 |
| 5 | — | 7 |
| 9 | 0 | 6 |
| 9 | 0 | 7 |
| 9 | 0 | 8 |
| 9 | 0 | 9 |
| 4 | 0 | 5 |
| 3 | — | 7 |

The compounds of the formula I3 are obtained analogously from 2-(4′-alkoxy-2′-fluoro-4-biphenylyl)-5-hydroxypyrimidines (prepared from 4′-alkoxy-2′-fluoro-4-biphenylylcarbamidines in accordance with Example 1).

$C_mH_{2m+1}$—Q⁴—[phenyl]—[phenyl-F]—[pyridazine]—O—$C_nH_{2n+1}$

| m | Q⁴ | n |
|---|----|----|
| 8 | 0 | 7 |
| 8 | 0 | 8 |
| 6 | 0 | 6 |
| 5 | — | 3 |
| 5 | — | 7 |
| 9 | 0 | 6 |
| 9 | 0 | 7 |
| 9 | 0 | 8 |
| 9 | 0 | 9 |
| 4 | 0 | 5 |
| 3 | — | 7 |
| 11 | 0 | 6 |
| 6 | 0 | 11 |

EXAMPLE 2

0.1 mol of 2-(4-heptyloxy-2-fluorophenyl)-5-hydroxypyrimidine (prepared from 4-heptyloxy-2-fluorobenzamidine in accordance with Example 1) is dissolved together with 0.12 mol of pyridine in toluene and 0.1 mol of nonanoyl chloride is then added at room temperature. Stirring is then carried out for 12 hours and standard working-up is carried out. 2-(4-Heptyloxy-2-fluorophenyl)-5-nonanoyloxypyrimidine is obtained, C 65 I, Δε=−0.2.

The following esters of the formula I are obtained analogously:

$C_mH_{2m+1}$—Q⁴—[phenyl-F]—[pyrimidine]—O—CO—[H]—$C_nH_{2n+1}$

| m | Q⁴ | n |
|---|----|----|
| 8 | 0 | 3 |
| 8 | 0 | 5 |
| 8 | 0 | 7 |

-continued

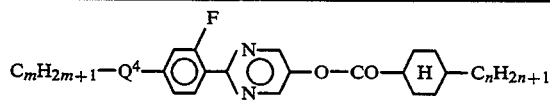

| m | Q⁴ | n |
|---|----|---|
| 8 | O  | 9 |
| 8 | O  | 10 |
| 8 | O  | 11 |
| 8 | —  | 3 |
| 8 | O  | 5 |
| 10 | — | 3 |
| 7 | O  | 7,  C 70 S$_c$ 133 S$_A$ 144 N 178.2 I, Δε = −0.2 |
| 7 | O  | 11 |
| 7 | —  | 3 |

EXAMPLE 3

A solution of 0.1 mol of 5-heptyloxy-2-(4-(2-hydroxy-5-oxaoctyloxy)-2-fluorophenyl)pyrimidine (prepared by heating optically active 1,2-epoxy-5-oxaoctane, obtainable from malic acid, with 5-heptyloxy-2-(4-hydroxy-2-fluorophenyl)pyrimidine in the presence of dry potassium carbonate and methyl ethyl ketone as solvent) in methylene chloride is cooled to −40° C. and 0.11 mol of DAST is added to it dropwise with moisture being excluded. The reaction mixture is then stirred for 12 hours while heating slowly to room temperature. Then hydrolysis is carried out with ice cooling and the reaction mixture is washed with dilute sodium hydroxide solution and several times with water. After drying over magnesium sulfate, the solvent is removed on a rotary evaporator and the crude product is purified chromatographically and by crystallization. Optically active 5-heptyloxy-2-(4-(2-fluoro-5-oxaoctyloxy)-2-fluorophenyl)pyrimidine is obtained.

The following compounds of the formula I1 are prepared analogously:

H$_{2m+1}$C$_m$─O─(CH$_2$)$_2$─*CH─CH$_2$─O─⟨phenyl-F⟩─⟨pyrimidine⟩─OC$_n$H$_{2n+1}$
                          |
                          F

| m | n |
|---|---|
| 2 | 7 |
| 4 | 7 |
| 5 | 7 |
| 2 | 8 |
| 3 | 8 |
| 4 | 8 |
| 5 | 8 |
| 3 | 9 |
| 3 | 10 |

EXAMPLE 4

By analogy with Example 3, 2-(4-octyloxy-2-fluorophenyl)-5-(2-fluoro-5-oxyoctyloxy)pyrimidine is obtained from 0.1 mol of 2-(4-octyloxy-2-fluorophenyl)-5-hydroxypyrimidine (prepared in accordance with Example 1) and 0.1 mol of optically active 1,2-epoxy-5-octane.

The following compounds of the formula II are prepared analogously:

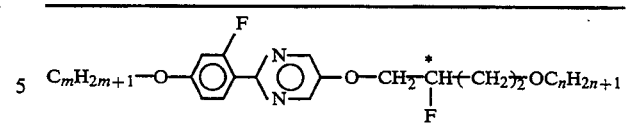

| m | n |
|---|---|
| 7 | 3 |
| 9 | 3 |
| 11 | 3 |

EXAMPLE 5

0.17 mol of diethyl azodicarboxylate (DEAD) dissolved in THF is added to a solution of 0.15 mol of 2-(4-decyloxy-2-fluorophenyl)-5-hydroxypyrimidine (prepared in accordance with Example 1), 0.17 mol of ethyl L(−)-lactate and 0.15 mol of triphenylphosphine in 400 ml of THF. In this process, a reaction temperature of 50° C. should not be exceeded. Stirring is carried out for 1 hour at 50° C. and then overnight at room temperature. Then the solvent is distilled off, the residue is dissolved in hot toluene and the solution is then slowly allowed to cool. The triphenylphosphine oxide precipitated is filtered off by suction, the filtrate is evaporated down and the residue is chromatographically purified. 2-[2-(4-Decyloxy-2-fluorophenyl)pyrimidine-b 5-oxy]propionethyl [sic] ester is obtained.

EXAMPLE 6

Optically active benzyl lactate is etherified by means of diethyl azodicarboxylate (DEAD)/triphenylphosphine with 2-(4-octyloxy-2-fluorophenyl)-5-hydroxypyrimidine (prepared in accordance with Example 1) and the benzyl group is then split off hydrogenolytically. The acid so obtained is converted as usual into the nitrile (oxalyl chloride, ammonia, thionyl chloride). Optically active 2-(4-octyloxy-2-fluorophenyl)-5-(1-cyanoethoxy)-pyrimidine is obtained.

EXAMPLE 7

A solution of 0.1 mol of DCC in methylene chloride is added at 0° C. to a mixture of 0.1 mol of 2-(4-octyl-2-fluorophenyl)-5-hydroxypyrimidine (prepared in accordance with Example 1), 0.1 mol of optically active 2-chloro-3-methyl butyric acid (prepared from valine) and a catalytic amount of 4-(N,N-dimethylamino)pyridine in 250 ml of methylene chloride. Then the solution is allowed to stand for 12 hours at room temperature, the precipitate is filtered off by suction, the filtrate is worked up as standard and 2-(4-octyl-2-fluorophenyl)-5-pyrimidinyl 2-chloro-3-methylbutyrate is obtained.

The following examples relate to ferroelectric liquid-crystalline media.

EXAMPLE A

A liquid-crystalline medium is prepared consisting of:
5.8% (2-hexyloxyphenyl)-5-heptylpyrimidine
5.8% (2-octyloxyphenyl)-5-heptylpyrimidine
5.8% (2-decyloxyphenyl)-5-heptylpyrimidine
1.1% (2-p-octyloxyphenyl)-5-octylpyrimidine
1.1% (2-p-nonyloxyphenyl)-5-octylpyrimidine
1.1% (2-p-decyloxyphenyl)-5-octylpyrimidine
7.0%   2-(4-decyloxy-2-fluorophenyl)-5-dodecyloxypyrimidine
14.1% 2-(4-heptyloxy-2-fluorophenyl)-5-dodecyloxypyrimidine 14.1% 2-(4-decyloxy-2-fluorophenyl)-5-undecyloxypyrimidine
5.0% 2-(4-octyloxy-2,3-difluorophenyl)-5-nonylpyrimidine
5.0% 2-(4-heptyloxy-2,3-difluorophenyl)-5-nonylpyrimidine
5.0% 2-(4-nonyloxy-2,3-difluorophenyl)-5-nonylpyrimidine
18.0% 2-(4-hexyloxyphenyl)-5-hexyloxypyrimidine and
10 % optically active 2-[4-(2-fluorooctyloxy)-2,3-difluorophenyl]-5-heptylpyrimidine.

This medium has the following physical properties:
Phase transitions: C< −20 S$_C$* 59 Ch 72 I
Spontaneous polarization (20° C.): −13.1 nC/cm$^2$
Switching time (20° C.): 125 μs

EXAMPLE B

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyrimidine
10.1% 2-(4-heptyloxy-2-fluorophenyl)-5-dodecyloxypyrimidine
10.1% 2-(4-decyloxy-2-fluorophenyl)-5-undecyloxypyrimidine
10% 2-(4-octyloxy-2,3-difluorophenyl)-5-heptylpyrimidine
5% 2-(4-octyloxy-2,3-difluorophenyl)-5-nonylpyrimidine
5% 2-(4-heptyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyrimidine and
10% optically active 2-[4-(2-fluorooctyloxy)-2-fluorophenyl]-5-heptyloxypyrimidine.

This medium has an S$_C$* phase range of over 60° C. and a high spontaneous polarization.

EXAMPLE C

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-( 4-decyloxy-2-fluorophenyl )-5-dodecyloxypyrimidine
10.1% 2-(4-heptyloxy-2-fluorophenyl)-5-dodecyloxypyrimidine
10.1% 2-(4-decyloxy-2-fluorophenyl)-5-undecyloxypyrimidine
10% 2-(4-octyloxy-2,3-difluorophenyl)-5-heptylpyrimidine
5% 2-(4-octyloxy-2,3-difluorophenyl)-5-nonylpyrimidine
5% 2-(4-heptyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyrimidine and
10% optically active 2-(4-octyloxy-2-fluorophenyl)-5-(1-cyanoethoxy)pyrimidine.

This medium has an S$_C$* phase range of over 50° C. and a high spontaneous polarization.

EXAMPLE D

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyrimidine
10.1% 2-(4-heptyloxy-2-fluorophenyl)-5-dodecyloxypyrimidine
10.1% 2-(4-decyloxy-2-fluorophenyl)-5-undecyloxypyrimidine
5.0% 2-(4-octyloxy-2-fluorophenyl)-5-dodecyloxypyrimidine
10% 2-(4-octyloxy-2,3-difluorophenyl)-5-heptylpyrimidine
5% 2-(4-octyloxy-2,3-difluorophenyl)-5-nonylpyrimidine
5% 2-(4-heptyloxy-2,3-difluorophenyl)-5-nonylpyrimidine
18% 2-(p-hexyloxyphenyl)-5-hexyloxypyrimidine and
10% optically active 2-[4-(2-fluorooctyloxy)-2-fluorophenyl]-5-heptyloxypyrimidine.

This medium has a wide S$_C$* phase range and a high spontaneous polarization.

EXAMPLE E

A liquid-crystalline medium is prepared consisting of:
5.8% 2-(p-hexyloxyphenyl)-5-heptylpyrimidine
5.8% 2-(p-octyloxyphenyl)-5-heptylpyrimidine
5.8% 2-(p-decyloxyphenyl)-5-heptylpyrimidine
1.1% 2-(p-octyloxyphenyl)-5-octylpyrimidine
1.1% 2-(p-nonyloxyphenyl)-5-octylpyrimidine
2.2% 2-(p-decyloxyphenyl)-5-octylpyrimidine
5.0% 2-(4-decyloxy-2-fluorophenyl)-5-dodecyloxypyrimidine
10.1% 2-(4-heptyloxy-2-fluorophenyl)-5-dodecyloxypyrimidine
10.1% 2-(4-decyloxy-2-fluorophenyl)-5-undecyloxypyrimidine
5.0% 2-(4-octyloxy-2-fluorophenyl)-5-dodecyloxypyrimidine
10% 2-(4-octyloxy-2,3-difluorophenyl)-5-heptylpyrimidine
5% 2-(4-octyloxy-2,3-difluorophenyl)-5-nonylpyrimidine
5% 2-(4-nonyloxy-2,3-difluorophenyl)-5-nonylpyrimidine
18% 2-(p-hexyloxyphenyl)-5-hexyloxypyrimidine and
18% optically active 2-[4-(2-fluorooctyloxy)-2-fluorophenyl]-5-heptyloxypyrimidine and
2% optically active 2-[4-(2-fluorooctyloxy)-2,3-difluorophenyl]-5-heptylpyrimidine.

This medium has a wide S$_C$* phase range and a high spontaneous polarization.

We claim:
1. A fluorophenylpyrimidine of formula Ib

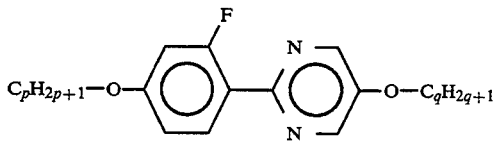

Ib wherein
the radicals $C_pH_{2q+1}$ and $C_qH_{2q+1}$ are straight-chain,
p is 5 to 14, and
q is 3 to 12,
and whereby the fluorophenylpyrimidine has a smectic mesophase.

2. A fluorophenylpyrimidine according to claim 1 having a smectic C phase.

3. A fluorophenylpyrimidine according to claim 2 which is :
2-(4-fluorophenyl)-5-nonyloxypyrimidine,
2-(4-fluorophenyl)-5-octyloxypyrimidine,
2-(4-fluorophenyl)-5-decyloxypyrimidine,
2-(4-fluorophenyl)-5-undecyloxypyrimidine,
2-(4-fluorophenyl)-5-dodecyloxypyrimidine,
2-(4-octyloxy-2-fluorophenyl)-5-octyloxypyrimidine,
2-(4-octyloxy-2-fluorophenyl)-5-nonyloxypyrimidine,
2-(4-octyloxy-2-fluorophenyl)-5-decyloxypyrimidine,
2-(4-octyloxy-2-fluorophenyl)-5-undecyloxypyrimidine,
2-(4-octyloxy-2-fluorophenyl)-5-dodecyloxypyrimidine,
2-(4-decyloxy-2-fluorophenyl)-5-octyloxypyrimidine,
2-(4-decyloxy-2-fluorophenyl)-5-nonyloxypyrimidine,
2-(4-decyloxy-2-fluorophenyl)-5-decyloxypyrimidine,
2-(4-decyloxy-2-fluorophenyl)-5-undecyloxypyrimidine,
2-(4-decyloxy-2-fluorophenyl)-5-dodecyloxypyrimidine,
2-(4-dodecyloxy-2-fluorophenyl)-5-octyloxypyrimidine,
2-(4-dodecyloxy-2-fluorophenyl)-5-nonyloxypyrimidine,
2-(4-dodecyloxy-2-fluorophenyl)-5-decyloxypyrimidine,
2-(4-dodecyloxy-2-fluorophenyl)-5-undecyloxypyrimidine, or
2-(4-dodecyloxy-2-fluorophenyl)-5-dodecyloxypyrimidine.

4. A ferroelectric liquid-crystalline medium containing at least two liquid-crystalline components, wherein at least one component is a fluorophenylpyrimidine of formula Ib according to claim 1.

5. A ferroelectric liquid-crystalline medium containing at least tow liquid-crystalline components, wherein at least one component is a fluorophenylpyrimidine of formula Ib according to claim 2.

6. A ferroelectric liquid-crystalline medium containing at least two liquid crystalline components, wherein at least one component is a fluorophenylpyrimidine of claim 3.

7. A liquid crystal display component containing a ferroelectric liquid-crystalline medium according to claim 4.

8. A liquid crystal display component containing a ferroelectric liquid-crystalline medium according to claim 5.

9. A liquid crystal display component containing a ferroelectric liquid-crystalline medium according to claim 6.

* * * * *